United States Patent
Maltby, Jr.

[11] Patent Number: 5,251,010
[45] Date of Patent: Oct. 5, 1993

[54] OPTICAL ROLLER WAVE GAUGE

[75] Inventor: Robert E. Maltby, Jr., Wayne, Ohio

[73] Assignee: Glasstech, Inc., Perrysburg, Ohio

[21] Appl. No.: 711,932

[22] Filed: Jun. 7, 1991

[51] Int. Cl.⁵ .............. G01B 11/30; G01N 21/86
[52] U.S. Cl. .................... 356/371; 356/239; 356/445; 250/571
[58] Field of Search .............. 356/371, 239, 445, 446, 356/448, 237, 430, 431, 384, 385; 250/571, 572, 559, 562, 563, 560, 561

[56] References Cited

U.S. PATENT DOCUMENTS

| | | | |
|---|---|---|---|
| 3,591,293 | 3/1970 | Maltby | 356/382 |
| 3,788,750 | 1/1974 | Maltby, Jr. et al. | 356/371 |
| 4,255,055 | 3/1981 | Schave | 356/371 |
| 4,585,343 | 4/1986 | Schave et al. | 356/445 |
| 4,781,465 | 11/1988 | Demachi et al. | 356/371 |
| 4,853,777 | 8/1989 | Hupp | 356/376 |
| 4,929,846 | 5/1990 | Mansour | 356/371 |
| 5,122,672 | 6/1992 | Mansour | 356/448 |

Primary Examiner—Richard A. Rosenberger
Assistant Examiner—Hoa Q. Pham
Attorney, Agent, or Firm—Brooks & Kushman

[57] ABSTRACT

An optical roller wave gauge for inspecting glass sheets processed on a horizontal roller hearth to determine roller wave distortion thereon includes a light source mounted to direct two parallel beams of light separated by a predetermined first distance onto the glass sheet, light detection means mounted to receive the two beams reflected from the surface of the glass sheet, first logic for determining the second distance between the beams at the light detection means, memory for storing a preselected number of second distances determined by the first logic, and second logic for retrieving the preselected number of stored second distances and generating a quality value representing the surface distortion on that portion of the glass sheet over which the preselected number of second distances was determined.

11 Claims, 3 Drawing Sheets

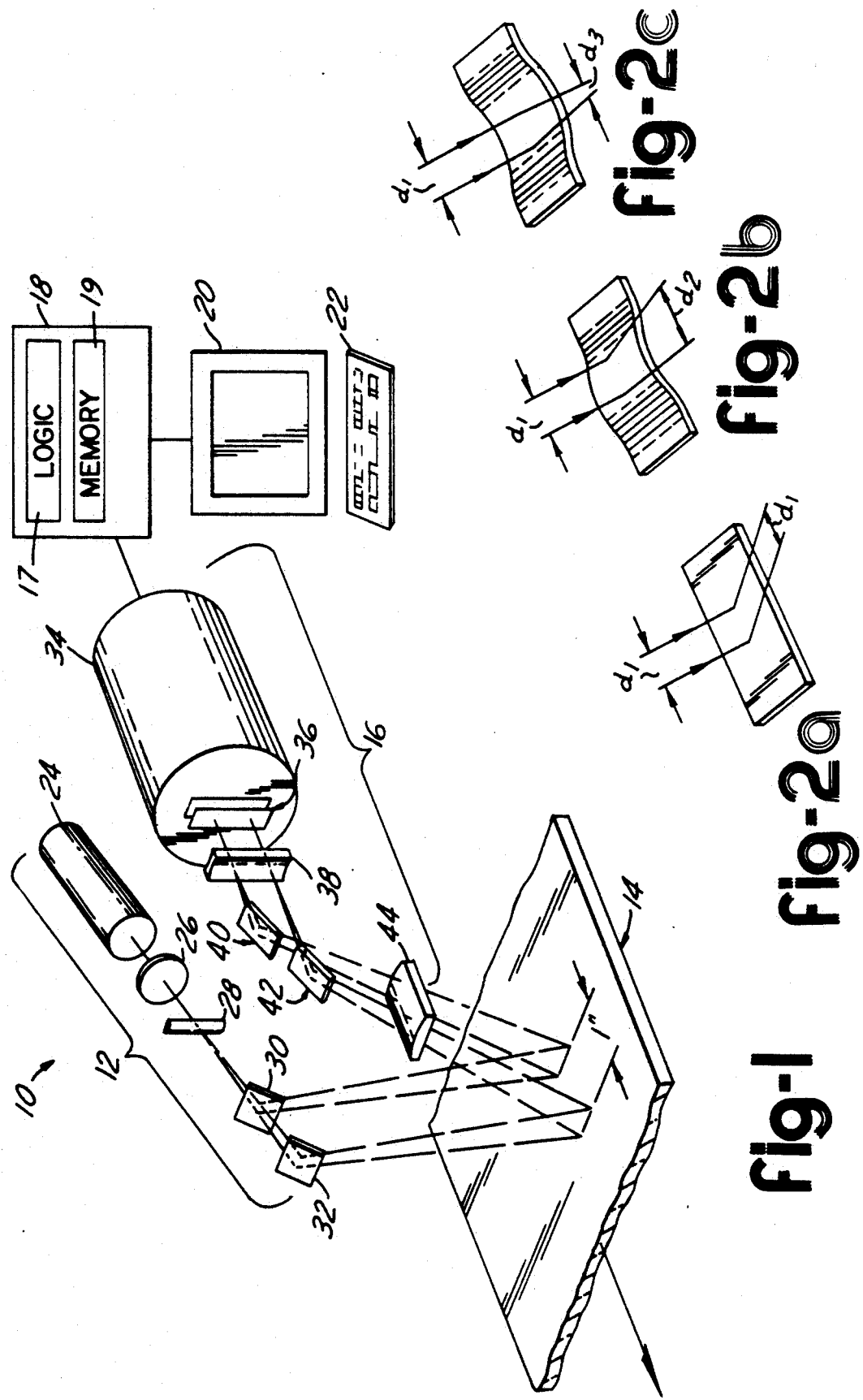

OPTICAL ROLLER WAVE GAUGE

TECHNICAL FIELD

The present invention relates generally to an apparatus for detecting surface distortion in glass sheets heated and otherwise processed on a horizontal roller hearth, and more particularly to an optical roller wave gauge which can be mounted directly on the roller hearth to inspect the glass sheets and provide data representing the amount of roller wave distortion on the glass sheets as the sheets are transported through the roller hearth.

BACKGROUND ART

One well known method of making glass sheets involves transporting the glass sheets through a furnace on a horizontal roller conveyor to heat the glass sheets to a temperature suitable for further processing of the glass sheets, such as bending and/or tempering or annealing. Since the glass sheets are typically heated to the softening point of the glass during these processes, conveyance and processing of the glass sheet may cause undesirable changes in the glass sheets, resulting in distortion in the images emitted or reflected by the glass when it is mounted, for example, in a building.

The distortion of images is typically caused by variations in the flatness of the glass surface. Isolated convex or concave lenses formed on the glass surface may cause distortion of images viewed through the glass and may render the glass unacceptable for architectural use.

One type of distortion commonly found in glass sheets processed on a roller conveyor hearth is a cylindrical sinusoidal wave of corrugation (or roller wave) resulting from deformation of the softened glass sheet as it is being supported by the rollers. It is desirable to quantify this characteristic in the glass in order to establish a quality standard for grading the glass during production, for example, to determine whether the glass has optics suitable for architectural use.

It is well known to provide optical inspection devices for measuring different characteristics of glass sheets. U.S. Pat. No. 3,591,293, issued to Maltby, Jr., et al. for an "Apparatus for Determining the Thickness of a Transparent Material by Measuring the Time Interval Between Impingement of Front and Back Surface Reflections on the Detector," utilizes a beam of light projected toward a glass surface and reflected from each of the opposite surfaces of the glass sheet toward and into a chopper assembly to continually monitor the thickness and/or width and position of a glass ribbon moving through the annealing end of a glass-making machine.

U.S. Pat. No. 3,788,750, issued to Maltby, Jr., et al. for "Inspecting Glass" discloses a method and apparatus for determining imperfections in flat glass sheets comprising a light source directing a pair of incident beams of light against the sheet when the sheet is supported on an inspection table, a chopper assembly for intercepting the reflected light beams and sequentially chopping the beams at a constant rate, and light sensitive means in the path of the chopped beams and producing an electrical signal of two pulses separated in time by an amount proportional to the spacing between the beam, and thereafter graphically recording the readings on a strip chart as an indication of position and focal length of lenses on the surface of the glass sheets.

U.S. Pat. No. 4,585,343, issued to Schave et al. for an "Apparatus and Method for Inspecting Glass", discloses an inspection apparatus for detecting surface distortion including a light source mounted to direct a beam of light toward the surface of the glass sheet, and a light detector mounted to receive the reflected beam and generate an output signal representing the width of the light pattern, which width is a function of the surface distortion of the sheet. This patent also discloses the use of a microcomputer connected to a display device.

While existing inspection devices provide some useful data on the characteristics and properties of glass sheets, none of the prior art devices provide the advantages of the present invention as is hereinafter more fully described.

SUMMARY OF THE INVENTION

An object of the present invention is to provide an optical roller wave gauge for a horizontal roller hearth glass sheet processing system which provides quantitative data related to roller wave distortion in a glass sheet as that glass sheet is being processed by the system.

Another object of the present invention is to provide an optical roller wave gauge that detects and provides data relating to roller wave distortion for batches of glass sheets produced on the system and stores the quantitative data for later review and comparison in analyzing the quality of glass sheet production on the system.

It is another object of the present invention to provide an optical roller wave gauge for a horizontal roller hearth glass sheet processing system which minimizes inaccuracies in data detection due to movement of the glass sheet surface in a direction other than the direction of conveyance of the glass sheet through the system.

It is still another object of the present invention to provide an optical roller wave gauge for a horizontal roller hearth glass sheet processing system which minimizes the inaccuracies in data detected by the gauge due to dust or other particles located on the surface of the glass sheet.

A further object of the present invention is to provide an optical roller wave guide for a horizontal roller hearth glass sheet processing system which minimizes inaccuracies in data detection as a result of variable light source intensity or interference of light from other sources.

A still further object of the present invention is to provide an optical roller wave gauge for a horizontal roller hearth glass sheet processing system which minimizes inaccuracies in data detection due to thermal refraction caused by index gradients in the air which, in turn, are caused by thermal gradients in the air.

A further object of the present invention is to provide an optical roller wave gauge which minimizes inaccuracies in data detection due to interference from light reflected from the second surface of the glass sheet.

According to the present invention, an apparatus for inspecting glass sheets to determine the surface distortion thereon is provided including a light source mounted to direct two parallel beams of monochromatic light separated by a predetermined first distance onto the upper surface of the glass sheet, light detection means mounted to receive the two beams reflected from the surface of the glass sheet, first logic means for determining the second distance between the beams at the light detection means, memory means for storing a preselected number of second distances determined by the first logic means, and second logic means for retrieving the preselected number of stored second distances and generating a quality value representing the surface distortion on that portion of the glass sheet over which the preselected number of second distances was determined.

The light source for the roller wave gauge preferably includes a low power laser, a spherical lens mounted immediately downstream from the laser to minimize the divergence in the light beam generated by the laser, a cylindrical lens mounted immediately downstream of the spherical lens for shaping the beam into a rectangular cross-section, and a 50/50 beam splitter and mirrors for generating two parallel light beams which may be directed onto the upper or first surface of a glass sheet as it is conveyed from the furnace, quench or other processing on the system.

The light detection means includes a line scan camera having a photosensitive linear array onto which the reflected beams may be directed, and a piece of optically ground glass immediately upstream from the linear array for slightly scattering the light from each of the beams transmitted therethrough. As will be appreciated by those skilled in the art, the ground glass will only slightly blur the image beams, yet it substantially reduces or eliminates any interference pattern from the images of each of the reflected beams on the linear array resulting from light reflected from the second surface of the glass sheet which is also transmitted in the path of the reflected beams.

The detection means preferably includes a filter located downstream from the ground glass. The filter should be suitable for passing only that wave length of light produced by the laser, thereby minimizing inaccuracies in data detection due to unwanted detection of light from sources outside the system.

The detection means also preferably includes a cylindrical lens mounted in the paths of the reflected parallel beams for focusing the image of the beams on the linear array.

The detection means also includes a pair of mirrors, each mounted to direct one of the reflected parallel beams through the filter, the ground glass, and onto a preselected position on the linear array. The mirrors are preferably provided with an adjusting mechanism which allows the angle of one mirror to be adjusted relative to the other mirror to direct the two beams reflected from a known flat surface to preselected positions on the linear array.

The optical roller wave gauge of the present invention also includes logic for periodically generating a signal representative of the distance between the images of the reflected beams detected at the linear array, and memory means for storing these distance signals.

The preferred embodiment further includes second logic means for receiving the stored signals for a predefined number of readings and generating a value from that group of stored signals representative of the roller wave distortion for that portion of the glass over which the group of readings was taken. The second logic means preferably also includes logic for converting the generated value to a quality number representing the "roller wave quality" for that portion of the sheet for which the value was generated. This quality member may be based upon preselected criteria assigned over the range of possible values by the user on the basis of qualitative inspection of glass having known distortion values.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 is an optical schematic and block diagram of the present invention;

FIGS. 2A-2C are schematic diagrams illustrating how variations in the flatness of the surface of an inspected glass sheet causes variations from the otherwise parallel reflection of the parallel source beams resulting in variation in the distance between the two beams at the point of reception on the linear array;

BEST MODE FOR CARRYING OUT THE INVENTION

Figure 3:
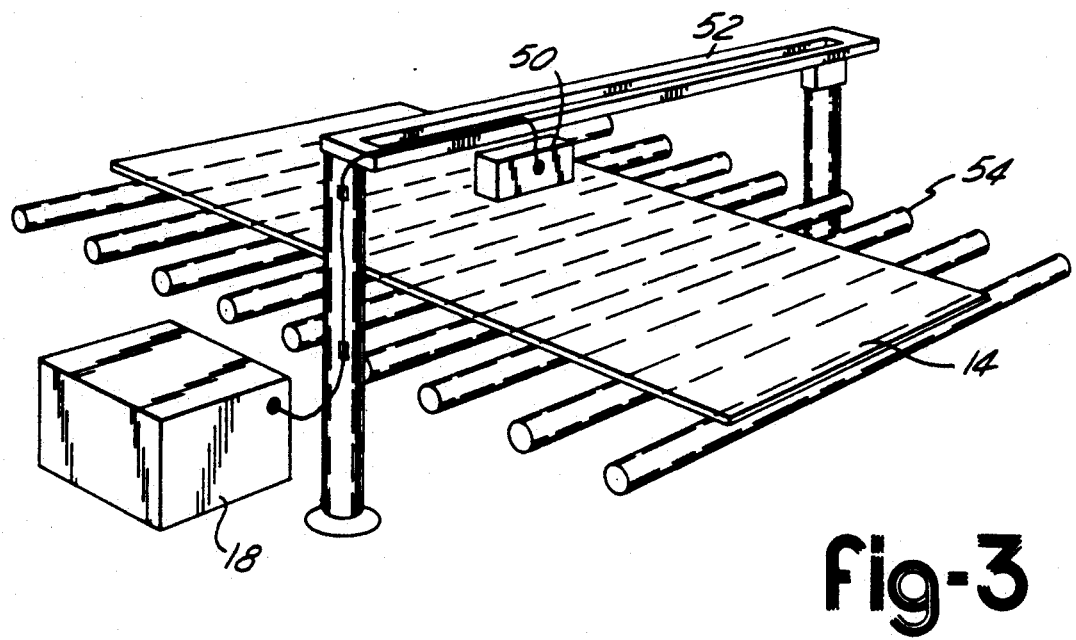
FIG. 3 is a perspective view of the optical roller wave gauge installed for operation in a horizontal roller hearth glass tempering system.

Referring to FIG. 1 of the drawings, an optical roller wave gauge in accordance with the present invention is generally indicated by 10. This optical roller wave gauge 10 includes a light source generally indicated by 12 mounted to direct two parallel beams of monochromatic light separated by a predetermined distance onto the surface of a glass sheet 14 conveyed on rollers below the light source 12. The optical roller wave gauge further includes light detection means generally indicated at 16, also mounted above the glass sheet 14, for receiving the two beams reflected from the surface of the glass sheet 14.

The optical roller wave gauge includes logic 17, shown schematically as part of a computer 18 including first logic means for determining the distance between the images of the reflected beams projected onto the linear array (also referred to hereafter as the second distance). Memory 19, also shown schematically in computer 18, is provided which is suitable for storing a preselected number of second distances determined by the first logic means for subsequent analysis, as well as for reporting, if desired.

Display means 20 such as a video monitor, is preferably provided to allow the operator to view selected data output by the roller wave gauge for each of a selected number of previously inspected glass sheets and/or glass sheet portions.

A data input device 22 such as a conventional keyboard may also be provided to allow the operator to directly input various configuration information as hereinafter described.

As illustrated in FIG. 2A, the parallel beams transmitted by the light source 12 onto the glass sheet 14 would be reflected in parallel from a flat surface on the top of the glass. Under those ideal circumstances, the distance d1 between the beams at transmission will also be the distance d1 between the images of the beams at the light detection means 16.

When the parallel beams are reflected from a convex (rather than flat) surface on the glass sheet, as shown in FIG. 2B, the reflected light beams will diverge, resulting in the distance d2 between the images at the light detection means 16 being relatively greater than the distance d1 between the transmitted beams.

Conversely, if the beams are transmitted onto a concave surface on the glass sheet 14 as shown in FIG. 2C, the reflected beams will tend to converge, resulting in a smaller distance d3 between the images of the beams detected by the light detection means 16. Thus, the change in the second distance between the beams reflected from the first (transmitted) distance is a function of the surface distortion on that portion of the surface from which the parallel beams are reflected.

Referring again to FIG. 1, the roller wave gauge of the present invention preferably includes second logic means for retrieving a preselected number of stored second distances and generating a quality value representing the surface distortion on that portion of the glass sheet over which the preselected number of second distances was determined.

In the preferred embodiment, the operator may assign, by percentages, the portions of each of three sections for each glass sheet intended to correspond to the leading edge, middle portion, and trailing edge of the glass sheet. Logic is provided to retrieve that percentage of the second distances detected for each defined portion and perform the following analysis on that data:

Center Section Average

The software logic calculates the average second distance for the center portion of the glass sheet. This is used as the value corresponding to a flat surface.

Total Deviation

The system then determines the total deviation from the flat surface value for each of the leading edge, center portions, and trailing edge portions of the glass sheet. If, for example, five data points are retrieved for the leading edge portion, with values of 605, 620, 609, 589 and 586, the average value would be 609 and the total absolute deviation for the leading edge of the sheet would be 58. This value corresponds to the magnitude of the roll wave in each section. In addition, this number may also indicate the extent of other distortion found in the leading and trailing edges of the glass sheet.

Maximum Deviation

The system then determines the maximum deviation between two consecutive readings for each of the leading edge, center and trailing edge portions. This corresponds to how quickly the glass surface changes from convex to concave, or vice-versa. Again, for example, the maximum deviation for the above leading edge would be 20.

In the preferred embodiment, total deviation and maximum deviation values for each portion are converted to a single quality number for that portion of the glass sheet, which quality number is then displayed along with the quality numbers for the other portions of the glass sheet. These quality numbers may, for example, range from 0 to 9 and relate to the calculated total and maximum deviation values on the basis of a correlation table prepared by the operator during set-up of the optical roller wave gauge. Following the above example data, the two leading edge values may be combined to form a composite value of 81. Reference to a user defined correlation table for leading edge values might indicate that a value of 81 is regarded as "3." Thus, by allowing the operator to assign arbitrary quality values to selected ranges of the total and maximum deviation data for the leading edge of the glass sheet on the basis of the user's off-line qualitative examination of leading edge portions of glass sheets having known total and maximum deviations values, the quality number will have a correlation to the objective data detected by the gauge as well as the optical quality perceived as a result of human inspection of the glass.

It should be noted that separate correlation tables of quality numbers to total and maximum deviation data can be created which are different for each of the leading edge, center and trailing edge portions of the glass sheet. For example, relatively greater total deviation and maximum deviation from flatness may be acceptable (e.g., a "5") quality number on the leading edge of a glass sheet, and at the same time, be unacceptable (e.g., a "2") if that amount of deviation, and thus distortion, is detected in the central portion of the glass sheet.

The system in the present invention may also include logic for retrieving other information detected by other sensing devices utilized by the glass sheet roller hearth for correlation of the conditions detected by those devices with data analyzed for particular glass sheets. For example, in the preferred embodiment, logic for retrieving temperature data collected from a commercially available radiation pyrometer temperature sensing device is employed to retrieve the temperature data for a particular glass sheet, correlate that data with the data generated by the optical roller wave gauge 10 and display the temperature data and quality value for that glass sheet simultaneously. In this manner, the system operator can view the correlation, if any, of trends in the quality values and corresponding surface temperatures for a series of glass sheets. In the preferred embodiment, the temperature data from the radiation pyrometer is correlated with the data collected by the roller wave gauge 10 for a particular glass sheet by assigning a time to each of the radiation pyrometer temperature values stored and, on the basis of an assumed conveyor speed (preprogrammed by the operator), correlating the data from the radiation pyrometer that is nearest in time to the calculated travel time for a glass sheet conveyed by the system to its corresponding roller wave gauge data.

Referring again to FIG. 1, the light source 12 preferably includes a low power continuous laser 24. In the preferred embodiment, a 0.5 milliwatt helium neon HeNe (6328 angstrom wavelength) laser, available from Aerotech, Inc., is utilized for this purpose. The light source 12 also includes a commercially available spherical lens 26, having a focal length of approximately 1 meter mounted immediately downstream from the laser 24. Thus, any divergence in the beam produced by the laser 24 is minimized by the spherical lens 26. The light source 12 also preferably includes a cylindrical lens 28 having a focal length suitable to create a rectangular cross section in the beam transmitted therethrough. The cylindrical lens is located immediately downstream from the spherical lens and preferably creates a rectangular cross-section in the beam of 0.5–0.75 inches X 0.04–0.05 inches.

It will be appreciated by those skilled in the art that the use of a rectangular or slit image for each of the beams rather than, for example, a point or circle cross-section, minimizes the likelihood of bad data for a particular point where dust or other particles on the glass sheet surface might cause the beam to be obscured or redirected.

A beam splitter 30 and mirror 32 are located further downstream in the light source 12 and are mounted to split the beam into two beams of equal intensity and direct the beams in a parallel relationship onto the surface of the glass 14. In the preferred embodiment, a 1 inch$^2$ 50/50 beam splitter and 1 inch$^2$ aluminum surface mirror, each having a two plane adjustment mechanism, available from Edmond Scientific, are utilized for this purpose. The beam splitter 30 and mirror 32 are preferably mounted to create parallel beams equal in intensity having approximately 1 inch beam spacing at the surface of the glass sheet 14.

The light detection means 16 preferably includes a line scan camera 34, ground glass 36, a filter 38, a pair of mirrors 40,42, and a second cylindrical lens 44 each mounted to intercept the reflected beams and direct the beams onto the linear array.

In the preferred embodiment, an Allen Bradley line scan camera, Catalog No. 2802-CAM 1 was utilized for the camera 34. The ground glass 36 was commercially available optical quality ground glass and is preferably located approximately ⅛ inch from the linear array on the camera 34. A red filter 38, a commercially available item, was selected because it passes only light having a wave length (6328 angstroms) corresponding to the wave length of the light beams generated by the laser 24. The filter 38 is preferably located approximately ½ inch from the linear array on the camera 34.

It will be appreciated by those skilled in the art that use of this filter minimizes the potential degradation of data due to unwanted transmission of light onto the linear array from other sources. It will also be appreciated by those skilled in the art that the use of the ground glass very close to the linear array causes a scattering of the transmitted beams sufficient to obscure any interference lines resulting from light reflected from the second surface of the glass in the paths of the reflected beams.

Referring to FIG. 3, the light source 12 and light detection means 16 are preferably mounted in a dust-free box 50 which in turn is mounted on rails 52 which span the roller conveyor 54 at the end of a horizontal roller hearth furnace. The light source 12 and light detection means 16 are suitably connected via conventional wiring to the computer 18 or other logic and memory means.

In the preferred embodiment, the second distances are acquired and stored by logic located in the Allen Bradley 2802-CAM 1 line scan camera 34, while the memory in the second logic for performing the remaining data analysis, display and storage are incorporated in a suitably programmed microcomputer. The microcomputer utilized in the preferred embodiment was an 80386AT Industrial Work Station, sold by Comarc, Inc. As will be appreciated by those skilled in the art, this Work Station is IBM compatible and other compatible microcomputers may be substituted for this purpose.

It will be noted by those skilled in the art, and by reference to the operating manuals for the Allen-Bradley 2802-CAM 1 line scan camera, that the camera 34 allows for preselected threshold settings which establish for the logic the conditions under which a particular sensor is illuminated. Since the distance between the images is being calculated, the logic in the camera 34 can be programmed to count the number of sensors that are illuminated across the width of one of the images, and determine the center point of the width of illuminated sensors. By similarly determining the center point of the other image, the second distance can be reliably calculated therefrom. As will be appreciated by those skilled in the art, these adjustable thresholds allow the operator to fine-tune the ability of the linear array to detect the images if, for example, the illumination for the system is reduced. Also, the fact of relatively lesser illuminated sensors on the fringe of each of the images has less impact on the derived second distances, since each of the images are likely to be at the same illumination level and since the second distance may be calculated from the center lines of the images rather than measured from the less reliably illuminated edges of the images.

The box 50 containing the light source 12 and light detection means 16 is preferably made from aluminum plate and is maintained under positive pressure by including a small air intake fan (not shown) mounted in a filtered opening (not shown), thereby preventing ingress of any dust or other particles through the other openings 60,61 in the box 50. The box 50 is also preferably mounted to be slidably positioned across the rails over the entire width of the conveyor 54 so that readings may be taken along any selected point on the width of the glass sheets.

A light emitting diode (not shown) is mounted over the conveyor to direct a light beam on the surface of the conveyor so that a glass sheet conveyed on the conveyor to the point of interrupting the light beam transmitted by the light emitting diode has also reached the point on the conveyor at which the parallel beams of the optical roller wave guide 10 are directed on the glass sheet's surface for data collection. The interruption of the light emitting diodes beam by the leading edge of the glass sheet is signaled via a suitable connection to the computer 18 to signal the start of a new glass sheet. Similarly, passage of the trailing edge of the glass sheet 14 which allows the beam transmitted from the light emitting diode to be transmitted without interruption is signaled to the computer 18 signifying the end of the glass sheet. As will be appreciated by those skilled in the art, this is one method for determining the correspondence of data collected by the optical roller wave guide to particular glass sheets. Data so identified can then be stored for later processing by the computer 18 as a group corresponding to a glass sheet, and/or further subdivided as described above into leading edge, center, and trailing edge data.

Figure 5:
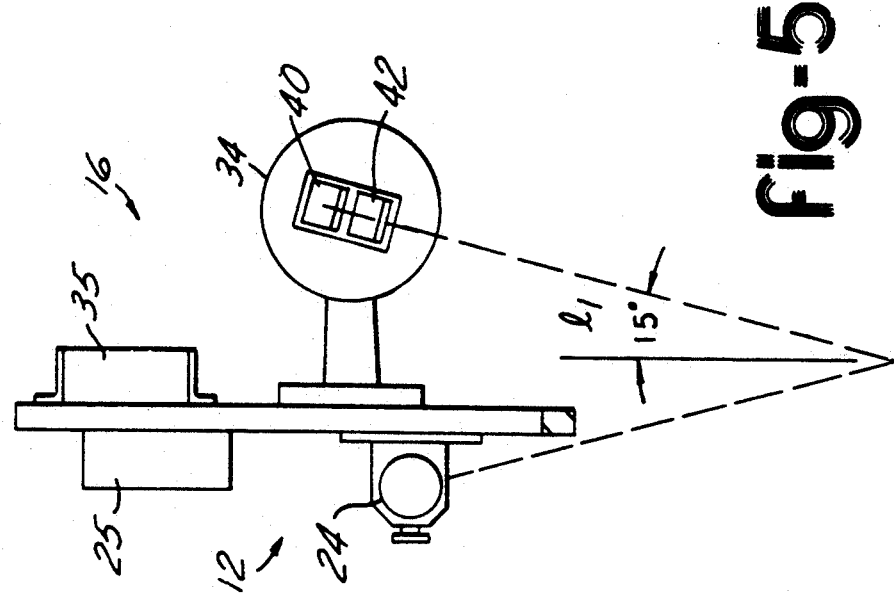
FIG. 5 is a fragmentary end view of the mounting board taken along lines 5—5 of FIG. 4.
Figure 4:
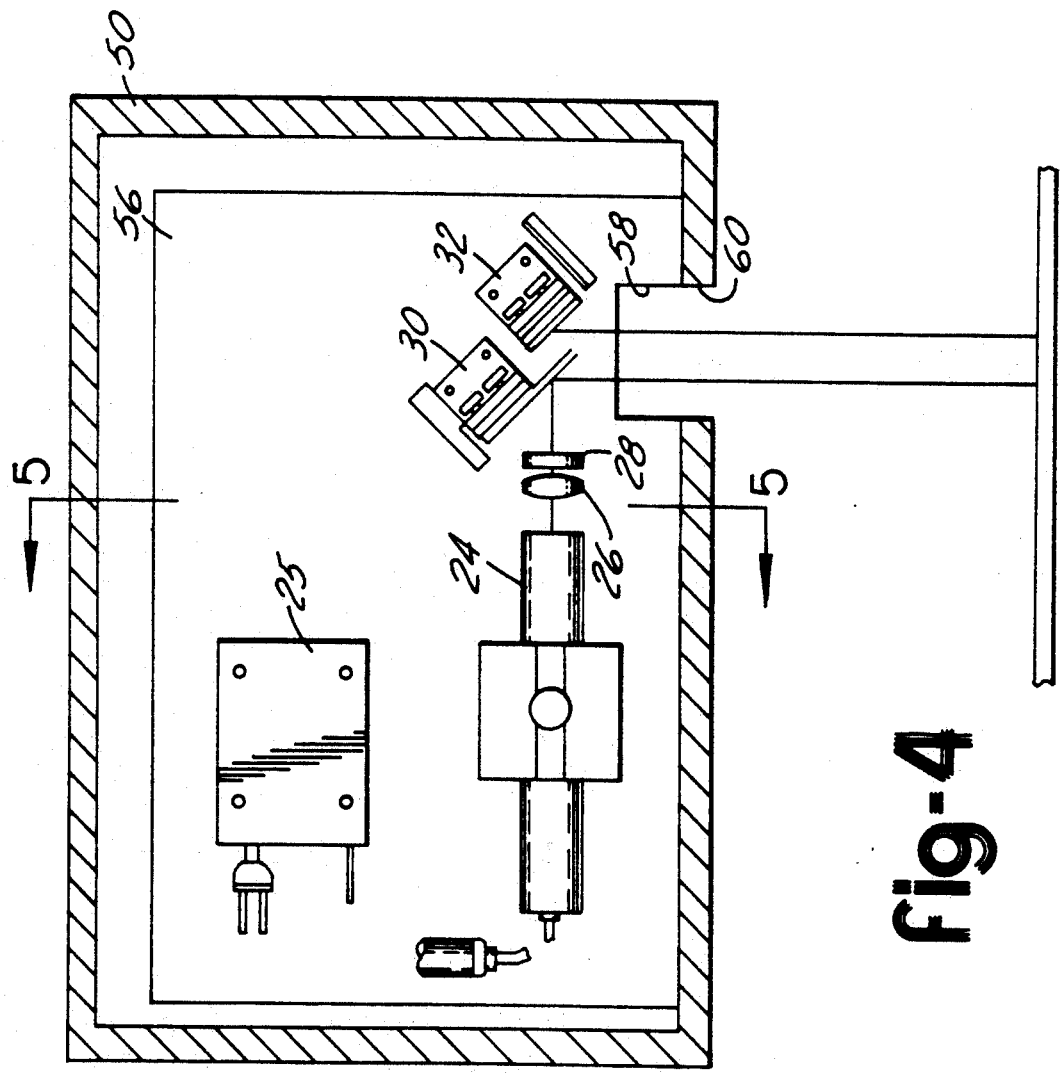
FIG. 4 is a partial cross-sectional view taken along lines 4—4 of FIG. 3 showing the mounting board for the light source and light detection means of the present invention.

Referring to FIG. 4, the light source 12 is mounted on a mounting board 56 within the box 50. The mounting board 56 is preferably ½ inch aluminum sheet. As can be seen from FIGS. 4 and 5, the laser 24, laser power supply 25, spherical lens, cylindrical lens, beam splitter 30 and mirror 32 are mounted on the board 56. The beam splitter 30 and mirror 32 are preferably positioned to direct the beams over a distance of about 8 inches to the glass surface at an angle of about 15° from a line 1, perpendicular to the glass surface so the beams are reflected from the glass sheet to the light detection means 16 mounted on the opposite side of the mounting board 56. As will be appreciated, the roller wave guide 10 may be mounted so that the distance over which the beam travels from the beam splitter 30 and mirror 32 can be varied from as close as 2⅜ inches to as far as 24 inches. However, these variations will affect the sensitivity of the system.

A rectangular cut-out 58 is cut from the mounting board 56 to accommodate the angular displacement in the beam. Additional cut-outs 60 and 61 (shown in FIG. 6) on the underside of the box 50 are also provided in the general location of the paths of the parallel beams transmitted by the light source 12, as well as the reflected beams received by the light detection means 16.

Figure 6:
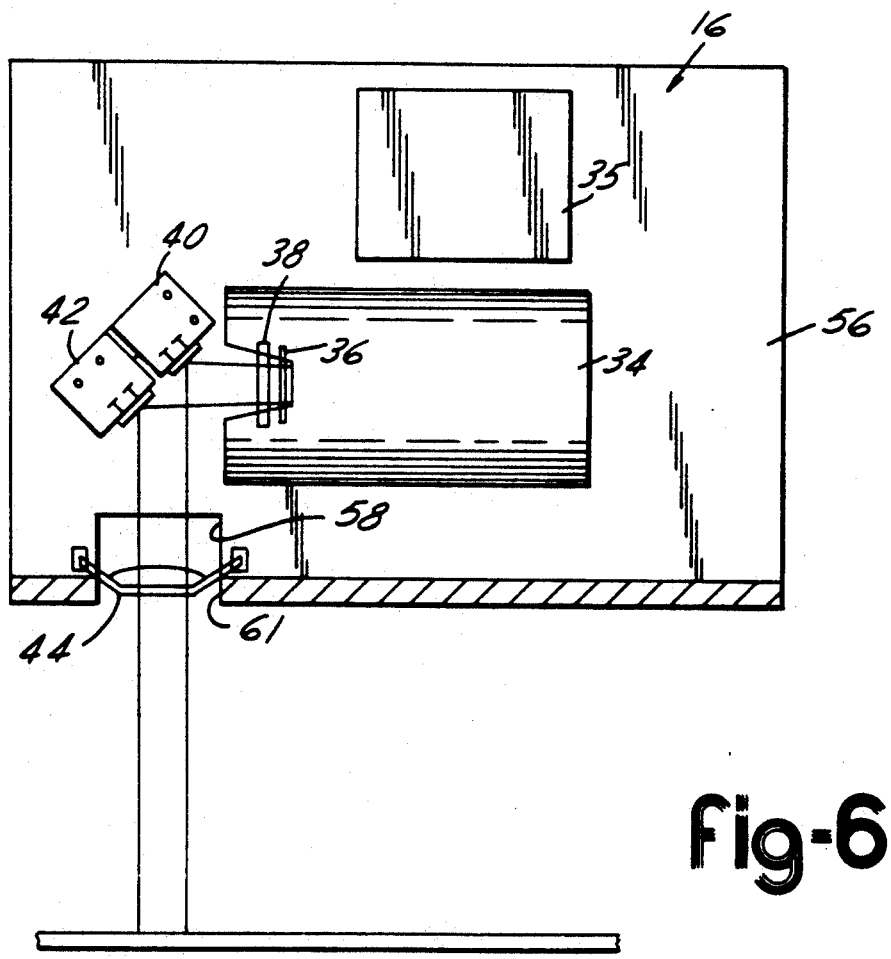
FIG. 6 is a fragmentary view taken along lines 6—6 of FIG. 3 showing the opposite side of the mounting board containing the light detection means utilizing the present invention.

As shown in FIG. 6, each of the components of the light detection means 16 are mounted on the mounting board 56 on the side opposite the light source 12. In particular, the linear array camera 34, an attendant power supply 35, ground glass 36, filter 38, mirrors 40,42 and cylindrical lens 44 are preferably mounted as shown. It should be noted that the cylindrical lens is preferably about 2.5×2.5 inches and is mounted at the midway point of the distance between the glass sheet surface and the linear array in the direction of the path travelled by the light beams. The cylindrical lens 44 preferably has a focal length of one-half the distance between the lens and the linear array so as to provide a focused image of the beams at the plane of the linear array.

It will be appreciated by those skilled in the art that mounting the light source 12 and light detection means 16 on a single mounting board 56 minimizes the amount of recalibration which might otherwise be necessary due to movement of the components relative to each other during operation of the roller hearth.

It will also be appreciated by those skilled in the art that the use of a single laser beam as the light source minimizes the sensitivity to variation in light intensity as a result of fluctuating or diminishing power supply, since any variation in light intensity will be equal for each of the transmitted beams. Similarly, the use of a single light source from the laser 24 split by the beam splitter 30 and mirror 32 into two parallel beams minimizes sensitivity due to movement of the glass in a direction other than the direction of conveyance. Furthermore, any thermal refraction resulting from the temperature gradient in the air immediately above the glass surface as it travels under the optical roller wave gauge 10 is minimized also, since the light source transmits two parallel beams which are substantially similarly affected by any such thermal refraction.

In the preferred embodiment, each of mirrors 40 and 42 can be adjusted to alter the angle of reflection of one of the beams relative to the other to locate the images of the beams at any desired locations on the linear array of the camera 34. For example, in the preferred embodiment, the linear array has over 2,000 photocells from top to bottom. It is desirable to locate the uppermost of the beam images approximately ⅓ of the distance from the top of the linear array and the second of the beam images approximately ⅓ from the bottom of the linear array in order to allow for maximum convergence or divergence of the beams within the limits of the approximately 2,000 sensors located across the length of the linear array of the camera 34.

While the best mode for carrying out the invention has been described in detail, those familiar with the art to which this invention relates will recognize various alternative designs and embodiments for practicing the invention as defined by the following claims.

What is claimed is:

1. An apparatus for inspecting glass sheets transported on a horizontal roller conveyor to determine roller wave distortion on the glass sheets, the apparatus comprising:
   a light source, including,
     means for generating a monochromatic beam of light,
     means for shaping the beam into a slit image of rectangular cross-section,
     means for splitting the beam into a pair of beams of equal intensity spaced apart at a first distance, and
     means for directing the pair of beams onto a selected surface of the glass sheet as it is transported on the conveyor;
   light detection means mounted to receive the pair of beams reflected from the selected surface of the glass sheet including a photosensitive linear array, the light detection means including filtering means interposed in the paths of the reflected beams between the photosensitive linear array and the glass sheet, for allowing transmission of light over a limited range of wavelengths including the wavelength of the pair of beams, and means for scattering the light in the pair of beams mounted in the path of the beams between the surface of the glass sheet and the photosensitive array to obscure any interference fringes caused by reflection of light from a surface on the glass sheet other than the selected surface;
   first logic means for periodically determining a second distance between the reflected beams on the photosensitive array;
   memory means for storing a preselected number of second distances determined by the first logic means; and
   second logic means for retrieving the preselected number of stored second distances and generating a quality value representing the roller wave distortion as a function of the first distance and the second distances for that portion of the glass sheet over which the preselected number of second distances was determined.

2. The apparatus of claim 1 wherein the light source and light detection means are mounted on opposite sides of a single mounting board above the glass sheet conveyor.

3. The apparatus of claim 1 wherein the means for directing the pair of beams directs the pair of beams along parallel planes to be incident as a pair of parallel slit images on the selected surface of the glass sheet.

4. The apparatus of claim 1 wherein the first logic further includes logic for counting the number of sensors in the photosensitive array which are illuminated across the width of the slit image for each beam and determining the center point of the width of the slit image, and logic for determining the second distance by measuring the distance between the center points of each of the slit images of the beams.

5. The apparatus of claim 1 wherein the means for generating a monochromatic beam of light is a low power laser.

6. The apparatus of claim 1 wherein the means for shaping the beam is a cylindrical lens.

7. The apparatus of claim 1 wherein the means for splitting the beam into a pair of beams and the means for directing the pair of beams comprises a fifty/fifty beam splitter and a mirror.

8. The apparatus of claim 1 wherein the light detection means is a line scan camera.

9. The apparatus of claim 1 wherein the means for generating a monochromatic beam of light is a helium neon laser which generates a monochromatic beam of approximately 6328 angstroms, and the filtering means is a red filter passing only light having a wavelength of 6328 angstroms.

10. The apparatus of claim 1 wherein the means for scattering the light in the pair of beams is optical quality ground glass.

11. An apparatus for inspecting glass sheets transported on a horizontal roller conveyor to determine the surface distortion on the glass sheets, the apparatus comprising:

a light source including,
 a low power laser,
 a cylindrical lens mounted in the path of the light beam generated by the laser for shaping the beam into a slit image of rectangular cross section,
 a fifty/fifty beam splitter and a mirror for splitting the beam into a pair of beams of equal intensity spaced apart at a first distance, and for directing the pair of beams along parallel planes onto a selected surface of the glass sheet;

light detection means mounted to receive the pair of beams reflected from the selected surface of the glass sheet including,
 a line scan camera having a photosensitive linear array,
 a filter interposed in the paths of the reflected light beams between the photosensitive linear array and the glass sheet for allowing transmission of light over a limited range of wavelengths including the wavelength of the pair of beams,
 ground glass interposed in the paths of the reflected light beams immediately adjacent the photosensitive linear array to obscure any interference fringes caused by reflection of light from a surface on the glass sheet other than the selected surface;

first logic means for periodically determining a second distance between the reflected beams on the photosensitive linear array;

memory means for storing a preselected number of second distances determined by the first logic means; and second logic means for retrieving the preselected number of stored second distances and generating a quality value representing the distortion as a function of the first distance and the second distances for that portion of the glass sheet over which the preselected number of second distances was determined.

* * * * *

UNITED STATES PATENT AND TRADEMARK OFFICE
CERTIFICATE OF CORRECTION

PATENT NO. : 5,251,010
DATED     : October 5, 1993
INVENTOR(S) : Maltby, Jr.

It is certified that error appears in the above-indentified patent and that said Letters Patent is hereby corrected as shown below:

On the Title Page, Item [57], line 6, delete "light detection means," and insert therefor —a light detector including a photo-sensitive linear array—.

Signed and Sealed this

Twenty-fourth Day of January, 1995

Attest:

BRUCE LEHMAN

Attesting Officer    Commissioner of Patents and Trademarks